United States Patent [19]

Syed et al.

[11] Patent Number: 4,602,648

[45] Date of Patent: Jul. 29, 1986

[54] PRE-SHAMPOO NORMALIZER FOR A HAIR STRAIGHTENING SYSTEM

[75] Inventors: Ali N. Syed, Hazelcrest; Kevin W. Gross, Chicago, both of Ill.

[73] Assignee: Soft Sheen Products, Inc., Chicago, Ill.

[21] Appl. No.: 666,427

[22] Filed: Oct. 30, 1984

[51] Int. Cl.$^4$ .............................................. A45D 7/00
[52] U.S. Cl. ........................................... 132/7; 424/70
[58] Field of Search .............................. 132/7; 424/70

[56] References Cited

U.S. PATENT DOCUMENTS

| | | | |
|---|---|---|---|
| 3,313,734 | 4/1967 | Lang et al. | 252/542 |
| 3,761,417 | 9/1973 | Parran, Jr. | 252/106 |
| 3,897,348 | 7/1975 | Atkinson | 252/8.75 |
| 3,912,808 | 10/1975 | Sokol | 424/71 |
| 3,986,825 | 10/1976 | Sokol | 8/406 |
| 4,027,008 | 5/1977 | Sokol | 424/62 |
| 4,175,572 | 11/1979 | Hsiung et al. | 132/7 |
| 4,228,810 | 10/1980 | Moore et al. | 132/7 |
| 4,237,910 | 12/1980 | Khahil et al. | 132/7 |
| 4,314,572 | 2/1982 | de la Guardia et al. | 132/7 |
| 4,324,263 | 4/1982 | de la Guardia | 132/7 |
| 4,373,540 | 2/1983 | de la Guardia | 132/7 |
| 4,390,033 | 6/1983 | Khalil et al. | 132/7 |
| 4,416,296 | 11/1983 | Meyers | 132/7 |
| 4,416,297 | 11/1983 | Wolfram et al. | 132/7 |

OTHER PUBLICATIONS

"Inolex Report Number 8, Protein", Inolex Chemical Company.
"Solan, Solan 50 & Lanexol AWS Alkoxylated Lanolins".
"Reten 300 Highly Cationic Liquid Polymer", Hercules Incorporation (No. 481-1).
"DL-Panthenol", Tri-K Industries, Inc.
"Tri-Stat IU (formerly Tri-Stat 115), Imidazolidinyl Urea", Tri-K Industries, Inc.
"CoVera", Costec, Inc.
"Lexein X350, Protein Hydrolysate", Inolex Chemicals.
"Natrosol Hydroxyethyl Cellulose—A Nonionic Water-Soluble Polymer", Hercules Incorporated.
"Ethoduomeen Polyethoxylated Diamines", Armak Chemicals.
"Mirataine CBS", Miranol Chemical Company, Inc.
Sykes & Hammes, "The Use of Merquat Polymers in Cosmetics", Merck Chemical Division, Calgon R&D.
"Versatility of Gafquat Polymers".
"Specifications of Standard Sonneborn Petrolatums, USP Grade".
"Sonneborn White Oils—Safe and Versatile Materials".
"Peptein 2000", George A. Hormel & Co.
"Arquad and Duoquad Quaternary Ammonium Chlorides", Akzo Chemic America, Armak Chemicals.
"Sodium Hydroxide NF Pelletts TAC", Mallinckrodt, Inc.
"Introduction Propylene Glycol, U.S.P.", Jefferson Chemical Co.
"Control Metal Ions with Chelating Agents—Versene Chelating Agents Handle Most Jobs", Dow Chemical Company.
"Glucamate Doe-120—A New Agent for Viscosity Enhancement", Amerchol Corporation.
"Lambs Tales—Polawax . . . Or Don't Trip on Your Bottom Line", Croda, Inc., Bulletin #68, Sep./Oct. 1977.
"Crodacols—Fatty Alcohols", Croda, Inc. (No. 8481).
"Technical Bulletin No. 267C, Monamid 716", Mona Industries, Inc. (Sep., 1973).
"TWEEN 20", ICI Americas Inc.
"Cosmetic Raw Materials and Suggested Formulations—Miranol C2M Conc.".
"Polychol Ethoxylated Lanolin Alcohols, Report 16".

*Primary Examiner*—Gregory E. McNeill
*Attorney, Agent, or Firm*—Allegretti, Newitt, Witcoff & McAndrews, Ltd.

[57] ABSTRACT

An improved hair straightening system based upon a pre-shampoo normalizer is disclosed. The improved system provides for rinsing the hair after the straightening composition has been applied to the hair for a sufficiently long period of time and then applying the pre-shampoo normalizer to the hair before the shampoo step. The pre-shampoo normalizer preferably includes between about 0.25 and about 10% by weight of a medium molecular weight cationic polymer, between about 2 and about 20% by weight of a hydrolyzed animal protein having a molecular weight of between about 200 and about 15,000 and less than about 10% by weight of a surface active agent. The pre-shampoo normalizer should also be adjusted to a pH of between about 2.5 and about 7 by using a conventional acid composition.

22 Claims, No Drawings

PRE-SHAMPOO NORMALIZER FOR A HAIR STRAIGHTENING SYSTEM

BACKGROUND OF THE INVENTION

This invention relates to an improved hair straightening system and a pre-shampoo normalizer for use in a hair straightening system.

Among the components of hair is a proteinaceous material called "keratin". The hair's keratin is made up of long fibrous polypeptide chains which are in turn formed from amino acids. The fibrous polypeptide chains are bonded together with horizontal cross bonds of two forms: hydrogen bonds and cystine bonds, also sometimes referred to as disulfide bonds.

Cystine bonds play an essential role in determining the degree of curl in hair. Straight or slightly wavy hair has very few cystine bonds and relies heavily upon hydrogen bonding to produce curl or waves in the hair. Very curly hair has a relatively larger amount of cystine bonds in the hair. While the hydrogen bonds can be broken merely by wetting the hair, such that straight or slightly wavy hair will lose virtually all body when wet, very curly hair maintains its body even when wet because the cystine bonds are relatively unaffected by water. Thus, very curly hair cannot be easily reset into new or different hair styles different from its natural state merely by wetting and shaping the hair.

In order to style very curly hair, the hair must first be straightened to some degree. This procedure is commonly referred to in the trade as "straightening" the hair. A composition employed to straighten the hair is similarly called a straightener or "relaxer." Straighteners have become increasingly popular in recent years with the emergence of hair styles that require straight or only slightly wavy hair.

The most important factor in hair straighteners is chemically breaking the cystine bonds so that the bonding sites may then slip past one another, permanently shifting their position and that of the polypeptide chains. The bonds may then be reformed at new bonding sites with the result that the hair assumes a relatively permanent straight position.

Alakline chemicals are typically used to break the cystine bonds. The alkaline chemicals also have the effect of softening and swelling the hair fiber. If the chemical is left on the hair for too long a period of time or if the chemical is too strong or too abundant, it may not break the cystine bond but also weaken or even dissolve the hair fiber. The outwardly visible sign of this type of chemical damage is destruction or breaking off of the hair.

There has been much discussion, often misleading, in recent literature about the pH of hair. Contrary to popular belief, hair has no intrinsic pH. However, the scalp and natural oils coat the hair fiber, giving its surface a slightly acidic pH of between about 4.5 and 5.5. In addition, hair has positive and negative charges which are balanced at a point known as the "iso-electric point." The iso-electric point generally falls in the range of about 5.0 to 6.5 on the pH scale.

Mildly acidic compounds, such as rinses and conditioners, etc., tend to shrink the hair fiber and flatten the cuticle, leading to a smoother appearance and reduction in comb drag. More strongly acidic compounds tends to have an increasingly damaging effect on hair. Similarly, mildly alkaline compounds swell and soften the hair fiber, permitting easier penetration of cosmetic ingredients into the hair. More strongly alkaline compounds are, again, damaging if left on the hair for too long and may even dissolve the hair.

It is believed that the most widely used chemical hair straightener currently employed is sodium hydroxide, although other compounds such as thioglycolates, bisulfides or other hydroxides, may also be used. Sodium hydroxide is a highly alkaline chemical and has various advantages in connection with straightening very curly hair; namely, fast processing time, good straightening, and more permanent straightness with less likelihood of reversion after shampooing. However, in view of the highly alkaline nature of sodium hydroxide, extreme care must be used in order to avoid damaging the hair, skin, or scalp. If the chemical is left on the hair for much longer than the recommended time, the hair can become brittle. In a brittle condition, the hair may be damaged by normal shampooing upon completion of the straightener treatment.

The prior art has taught various techniques for using selected compositions in a way that conditions the hair and reduces the risk of damage to hair as a result of contact with the straightener compositions. In addition to reducing the risk of damage, such compositions frequently add an aesthetic quality to the hair, e.g., easier combability, softer touch, higher sheen. For example, it has been known that cationic fatty quaternary compounds having fatty chain length of approximately 8–18 carbon atoms may help condition hair. However, since such cationic materials are usually inactivated by reaction with anionic surfactants, they have typically been employed as separate rinse treatments after shampooing. U.S. Pat. Nos. 3,313,734 and 3,761,417 purportedly describe improved conditioning compositions which could be incorporated into a shampoo. Such incorporation is said to minimize hair damage of shampooing following straightening because the conditioner would begin to contact the hair fiber before the hair had been seriously manipulated and damaged during the shampoo process. More recently, as taught by U.S. Pat. Nos. 3,912,808; 3,986,825; and 4,027,008, it was known that certain tertiary amine polymers and quaternary ammonium polymers could be incorporated directly into the straightening or hair treatment composition and, thus, could begin to condition the hair and reduce potential damage to the hair even before shampooing. Still later patents, for example, U.S. Pat. No. 4,175,572, disclosed that specific quaternary ammonium polymers could be employed in a wider range of straightener compositions having a higher pH than was previously known.

All of the known prior art techniques for reducing damage to the hair in a straightener system are very limited in their ability to prevent damage to the hair. Although prior art compositions have shown some utility in this regard, relaxers and hair straightening techniques are still plagued by problems of hair damage and introduction of a harsh or raspy feel to the hair. The present invention provides an improvement in hair straightener systems, further reducing the likelihood of damaged hair and further improving the hair styling that results from a hair straightening treatment.

SUMMARY OF THE INVENTION

Thus, an object of the present invention is to provide an improved hair straightening system and further to provide a pre-shampoo normalizer for use in a hair straightening system.

It is an object of this invention to provide improved conditioning to hair in a hair straightener system such that hair is made more tangle free, softer, and silkier to the touch.

A further object of the invention is to provide more body, sheen and manageability to the hair in a straightener treatment.

A still further object of the invention is to identify proteins and cationic polymers which are more substantive to the hair and, further, to identify a method by which these proteins and cationic polymers can be associated with the hair in a more advantageous manner.

A still further object of the present invention is to provide an improved formula and technique for neutralizing residual alkalinity of the hair after a straightener treatment.

The method of the present invention comprises applying to the hair a straightener compound that has chemical properties which are sufficient to break the cystine bonds in the hair. Following treatment with the straightener, the hair is rinsed to flush away a substantial portion of the straightener composition. Thereafter, a pre-shampoo normalizer composition is applied to the hair prior to shampooing. The pre-shampoo normalizer comprises, at a minimum, either (1) a protein of molecular weight between 200 and 15,000 or (2) a cationic species, or (3) a mixture of two, dispersed in water and adjusted to a pH of between 2.5 and 7 with an acid species. After treatment with the pre-shampoo normalizer, the hair is shampooed to remove any residual straightener compound as well as to remove excess pre-shampoo normalizer.

The preferred pre-shampoo normalizer composition of this invention generally comprises between about 0.25 and about 10% by weight of a medium molecular weight cationic polymer, between about 2 and about 20% by weight of a hydrolyzed protein having a molecular weight of between about 200 and about 15,000, and less than about 10% by weight of a surface active compound. In a highly preferred form of the pre-shampoo normalizer, the cationic polymer comprises between about 2 and about 4% by weight of the pre-shampoo normalizer; and the hydrolyzed protein is a hydrolyzed animal protein of average molecular weight between about 4,000 and about 5,000 and comprises between about 5 and about 10% by weight of the pre-shampoo normalizer. P Furthermore, the pH of the pre-shampoo normalizer lies between about 2.5 and about 7. The composition is most preferably slightly acidic with pH between about 4.0 and about 6.0. The pH may be adjusted with an acid composition that will neutralize any residual alkaline chemical used in the straightener composition. Hydrochloric acid is particularly preferred as the acid used to adjust pH.

The straightener composition initially applied to the hair in connection with the present inventive method may by any of the straighteners commonly known and available in the trade. Similarly, the shampoo employed in the inventive method after the pre-shampoo normalizer may be selected from those commonly known and employed in the trade.

DETAILED DESCRIPTION OF THE PREFERRED EMBODIMENTS

The method and composition of this invention comprise an improved hair straightening system, and also a pre-shampoo normalizer composition which is applied to hair after straightener treatment and before shampoo treatment. In one embodiment, the invention comprises a method of straightening hair in which a straightener composition is applied to the hair change chemical properties sufficient to react with cystine bonds in the hair keratin; to lanthionine bonds the hair is rinsed to flush away a substantial portion of the straightening composition; the pre-shampoo normalizer is applied comprising a protein of molecular weight between 200 and 15,000 or a cationic species, or both, in water at a pH between 2.5 and 7; and the hair is shampooed to remove any residual straightening composition as well as excess pre-shampoo normalizer. It has been found that proteins of the specified molecular weight range, and cationic species, are substantive to hair; that is, they are taken up by the hair. Applying the pre-shampoo normalizer at the stage after the straightener but before the shampoo minimizes the chance of damage to the hair due to physical manipulation in the shampoo stage. Surprisingly, the use of this pre-shampoo normalizer between the straightener and the shampoo treatments provides hair which is softer, more tangle free, and easier to manage than when conditioners, proteins and/or polymers are incorporated into either the straightener or the shampoo or applied after the shampoo. Another embodiment of the invention comprises the preferred pre-shampoo normalizer itself. The pre-shampoo normalizer composition mediates damage to the hair and enhances its aesthetic qualities following treatment with the straightener.

Hair is at a relatively high alkaline pH of between about 9 and 11 when the straightener is rinsed out of the hair. If the hair is shampooed with a shampoo at this stage, either an acidic or alkaline shampoo, the hair tends to become raspy in feel and can be damaged by hand manipulation during the shampoo. Incorporating conditioning and softening compounds into the straightener treatment or the shampoo can improve this situation, but they do not satisfactorily resolve it.

As an aspect of this invention, it has been found that the hair is at this stage particularly receptive to certain hydrolyzed proteins and cationic polymers. This invention has identified specific proteins and polymers which are particularly effective in treating the hair in its sensitive, high pH state after the straightener treatment.

The pre-shampoo normalizer of this invention comprises a cationic species, preferably between about 0.25 and about 10% by weight of a medium molecular weight cationic polymer; a hydrolyzed protein, preferably between about 2 and about 20% by weight of a hydrolyzed animal protein having a molecular weight of between about 200 and about 15,000, or more preferably, between about 500 and about 10,000; and less than about 10% by weight of a surface active agent. The pH of the pre-shampoo normalizer is preferably adjusted to a range of between about 2.5 and about 7.

Examples of non-polymeric cationic species which may be employed in the pre-shampoo normalizer include Dehyquart A available from Henkel, Arquad 2HT-75 from Armak, and Carsoquat SDQ-25 from Lonza. Cationic polymers which may be employed include Polymer JR-30M from Union Carbide, and Gafquat 755 from GAF.

In an especially preferred formulation, the cationic polymer comprises between about 2 and about 4% by weight of the pre-shampoo normalizer. Cationic polymers of medium molecular weight are preferred, because, it is believed, such polymers will be taken up by the alkaline swollen hair fiber more readily. The particularly preferred medium molecular weight cationic polymers include ethanaminium, N,N,N-trimethyl-2-[(2-methyl-1-oxo-2-propenyl)oxy]-, methylsulfate, homopolymer (($C_9H_{18}NO_2.CH_3O_4S)_x$), of molecular weight between about one million and about two million.

In a particularly preferred formulation, the hydrolyzed animal protein should comprise between about 5 and about 10% by weight of the composition and have a molecular weight of between about 4000 and 5000. Examples of suitable hydrolyzed animal proteins include Crotein SPA from Croda, Peptein 2000 from Hormel and Polypeptide SF available from Stepan. A particularly preferred hydrolyzed animal protein, sometimes referred as hydrolyzed collagen protein, is the material sold under the LEXEIN trademark by Inolex Chemicals of Chicago, Ill., for example, LEXEIN X250 and LEXEIN X350. LEXEIN X350 has been found to be an especially preferred collagen for this application. The LEXEIN proteins are hydrolized by enzymatic digestion, which produces a mixture of straight chain polypeptides in a relatively narrow molecular weight distribution around 4800. It is believed that these collagens are substantively absorbed into the hair fiber in a particularly effective manner.

The surface active agent or surfactant may comprise any amphoteric, anionic, cationic, or non-ionic detergent previously known and readily available in the art. Examples include Maprofix NH from Onyx, Miranol C2MSFConc available from Miranol, and Monoamid from Mona. Cocoamidoalkylammonium sulfonate (3-[(3-cocoamidopropyl)dimethylammonio]2-hydroxypropane sulfonate) has been found to be particularly advantageous. It is important that the level of surfactant not exceed about 10% by weight of the pre-shampoo normalizer, because it is believed that higher levels of surfactants interfere with the ability of the protein and polymer to be taken up by the hair fiber. Preferably, the concentration of the surface active agent will not exceed about 7%, and most preferably will not exceed about 5% by weight of the pre-shampoo normalizer.

Generally, the pre-shampoo normalizer is prepared by mixing the cationic species, the hydrolyzed protein, the surface active compound, and any other additives such as pH adjusters, preservatives or fragrance in an aqueous solution in the proper amounts to give the indicated concentrations. Individual cationic species or mixtures of species, individual proteins or mixtures of proteins, and individual surfactants or mixtures of surfactants may be employed to result in the total concentrations as specified herein.

As previously noted, the straightener composition initially applied to the hair in connection with the present invention may be any of the straighteners commonly known and available in the trade. Examples of such straighteners include sodium hydroxide and two phase guanidine hydroxide systems. See U.S. Pat. No. 3,912,808 issued in the name of Phillip E. Sokol on Oct. 14, 1975; U.S. Pat. No. 4,175,572 issued in the names of Hsiung and Mueller; and U.S. Pat. Nos. 4,416,296; 4,390,033; 4,373,540; 4,324,263; and 4,314,572. The straightener composition is initially applied to the head and worked into the hair with gentle massage. The straightener composition is allowed to stand thus for about 5-15 or 20 minutes, depending upon the degree of curl in the hair's natural state and the degree of straightness desired.

After the hair has been straightened to the desired degree, the hair is rinsed, preferably with water, to flush away a major portion of the straightener composition. In this way, the pre-shampoo normalizer and the hair straightener composition are not applied to the hair at the same time.

After the hair has been rinsed, the pre-shampoo normalizer is applied to the head and gently massaged into the hair, leaving it to stand on the hair for a period of one to several minutes depending upon the degree of straightness that has been created in the hair and on the relative health and strength of the hair. Generally speaking, in determining when the pre-shampoo normalizer has been left on the hair for a sufficiently long time, the beautician should look for four factors: porosity, elasticity, texture, and density of the hair.

Once the beautician has judged that the pre-shampoo normalizer has been left on the hair for a sufficient length of time, the hair may again be rinsed with water so as to flush away the excess pre-shampoo normalizer. Regardless of whether the hair is rinsed a second time after the pre-shampoo normalizer step, the hair is then shampooed to remove any residual straightener composition as well as excess pre-shampoo normalizer. As previously noted, any suitable shampoo may be used for this purpose. Examples of such shampoos include those disclosed in U.S. Pat. No. 3,761,417 issued to John Parran on Sept. 25, 1973, the disclosure of which is incorporated herein by reference. Since the pre-shampoo normalizer has now restored strength, porosity, elasticity, and density, as well as manageability, smoothness and combability to the hair, shampooing and the hand manipulations involved in shampooing will no longer cause damage or breakage to the hair.

In addition to the cationic species, hydrolyzed protein, and surface active agent, the pre-shampoo normalizer will advantageously include a variety of other additives and chemicals to assist and promote manufacture, stability, and overall aesthetic consumer appeal. Examples of such pre-shampoo normalizers follow:

TABLE I

| Ingredient | Formula 1 | Formula 2 | Formula 3 |
|---|---|---|---|
| Methyl p-hydroxybenzoate | 0.25 | 0.25 | 0.25 |
| N—(2-Hydroxyethyl)-N—Acetyl Ethanolamine | 7.00 | 7.00 | 1.00 |
| HCL (Conc.) | 2.00 | 2.00 | 2.00 |
| Polyethylene Glycol (60) Lanolin | 5.00 | 5.00 | 1.00 |
| Ethanaminium,N,N,N—Trimethyl-2-[(2-methyl-1-oxo-2-propenyl)oxy]-, Methyl Sulfate, Homopolymer | 3.00 | 3.00 | 3.00 |
| Panthenol | 1.00 | 1.00 | 0.50 |
| Imidazolidinyl Urea | 0.50 | 0.50 | 0.50 |
| Aloe Vera | 20.00 | 20.00 | 1.00 |
| LEXEIN X350 | 7.00 | 7.50 | 7.50 |
| N—(3-chloroallyl) Hexaminium Chloride | 0.25 | 0.25 | 0.25 |
| Hydroxyethyl cellulose | — | — | 0.75 |
| N,N',N'—tris(2-Hydroxyethyl)-N—tallow-1,3-diaminopropane | — | — | 4.00 |
| 3-[(3-cocamidopropyl) dimethylammonio]2-hydroxypropane sulfonate | — | — | 4.00 |
| Dehyquart A | — | 4.00 | — |
| Maprofix NH | — | 4.00 | — |
| Arquad 2HT-75 | 3.00 | — | — |
| Monamid 716 | 5.00 | — | — |
| H₂O | balance | balance | balance |

The pre-shampoo normalizers of Table I were prepared by mixing the water, methyl p-hydroxybenzoate and imidazolidinyl urea at room temperature. The hydroxyethyl cellulose was then dispersed in the mixture until a homogeneous gel was formed. The gel was then heated to 80° C. and maintained at that temperature while all further components were added, with the exception of the protein, the N-(3-chloroallyl) hexaminium chloride, and the hydrochloric acid. The mixture was an opaque amber up to this point. The composition was then cooled to 60° C. and the final three ingredients were added. (Upon addition of the acid the mixture turned clear and its viscosity decreased.) In general the pre-shampoo normalizer will have a light, clear amber color, a characteristic odor of proteins, and a pH of between about 4 and about 6.

From the foregoing, it is apparent that there is provided an improved pre-shampoo normalizer for a hair straightener system and an improved method of hair straightening. The above description relates to a preferred embodiment of the invention. Alternative formulations are, however, possible within the scope of the invention. Therefore, the subject matter of the invention is to be limited only by the following claims and their equivalents.

What is claimed is:

1. A method of straightening hair, comprising the following steps in combination:
   (a) applying to the hair a straightening composition with chemical properties sufficient to change the cystine bonds in the hair keratin to lanthionine bonds;
   (b) rinsing the hair to flush away a substantial portion of the straightening composition;
   (c) applying a pre-shampoo normalizer to the hair, said pre-shampoo normalizer having a pH of between 2.5 and 7 and comprising at least one component which is substantive to hair selected from the group consisting of a cationic species and a protein of molecular weight between about 200 and about 15,000;
   (d) shampooing the hair to remove any residual straightening composition that may remain after the rinsing step as well as excess pre-shampoo normalizer.

2. The method of claim 1 wherein the pre-shampoo normalizer comprises
   (i) between about 0.25 and about 10% by weight of a medium molecular weight cationic polymer;
   (ii) between about 2 and about 20% by weight of hydrolyzed animal protein having a molecular weight between about 200 and about 15,000; and
   (iii) less than about 10 percent by weight of a surface active compound.

3. The method of claim 2 wherein the cationic polymer comprises between about 2 and about 4 percent by weight of the pre-shampoo normalizer.

4. The method of claim 2 wherein the hydrolyzed animal protein comprises between about 5 and about 10 percent by weight of the pre-shampoo normalizer and has a molecular weight of between about 4000 and about 5000.

5. The method of claim 2 wherein the surface active compound comprises less than about 7.0 percent of the pre-shampoo normalizer.

6. The method of claim 2 wherein the pre-shampoo normalizer has a pH of between about 4 and about 6.

7. The method of claim 2 wherein
   (i) the cationic polymer comprises between about 2 and about 4 percent by weight of the pre-shampoo normalizer;
   (ii) the hydrolyzed animal protein has a molecular weight of between about 4000 and about 5000 and comprises between about 5 and about 10 percent by weight of the pre-shampoo normalizer;
   (iii) the surface active compound comprises less than about 5.0 percent of the pre-shampoo normalizer; and
   (iv) the pre-shampoo normalizer has a pH of between about 4 and about 6.

8. In a method for straightening hair by applying to the hair a straightening composition with chemical reducing properties sufficient to change the cystine bonds in the hair keratin, then shampooing the hair to remove at least a major portion of the straightening composition from the hair, the improvement comprising the steps of initially rinsing the hair to flush away a substantial portion of the straightening composition, then applying a pre-shampoo normalizer, said rinsing and applying steps to be performed after the straightening composition has been applied to the hair but before the hair has been shampooed, said pre-shampoo normalizer having a pH of between 2.5 and 7 and comprising at least one component which is substantive to hair selected from the group consisting of a cationic species and a protein of molecular weight between about 200 and about 15,000.

9. The method of claim 8 wherein the pre-shampoo normalizer comprises
   (i) between about 0.25 and about 10% by weight of a medium molecular weight cationic polymer;
   (ii) between about 2 and about 20% by weight of hydrolyzed animal protein having a molecular weight between about 200 and about 15,000; and
   (iii) less than about 10 percent by weight of a surface active compound.

10. The method of claim 9 wherein the cationic polymer comprises between about 2 and about 4 percent by weight of the pre-shampoo normalizer.

11. The method of claim 9 wherein the hydrolyzed animal protein comprises between about 5 and about 10 percent by weight of the pre-shampoo normalizer and has a molecular weight of between about 4000 and about 5000.

12. The method of claim 9 wherein the surface active compound comprises less than about 7.0 percent of the pre-shampoo normalizer.

13. The method of claim 9 wherein the pre-shampoo normalizer has a pH of between about 4 and about 6.

14. The method of claim 9 wherein
   (i) the cationic polymer comprises between about 2 and about 4 percent by weight of the pre-shampoo normalizer;
   (ii) the hydrolyzed animal protein has a molecular weight of between about 4000 and about 5000 and comprises between about 5 and about 10 percent by weight of the pre-shampoo normalizer;
   (iii) the surface active compound comprises less than about 5.0 percent of the pre-shampoo normalizer; and
   (iv) the pre-shampoo normalizer has a pH of between about 4 and about 6.

15. A pre-shampoo normalizer composition for maintaining and improving hair quality during straightening treatments comprising, in combination:

(i) between about 0.25 and about 10.0 percent by weight of a medium molecular weight cationic polymer;

(ii) between about 2.0 and about 20.0 percent by weight of hydrolyzed protein having a molecular weight of between about 200 and about 15,000; and (iii) less than about 10 percent by weight of a surface active compound.

16. The composition of claim 15 wherein the cationic polymer comprises between about 2 and about 4 percent by weight of the pre-shampoo normalizer.

17. The composition of claim 15 wherein the hydrolyzed protein comprises between about 5 and about 10 percent by weight of a hydrolyzed animal protein of molecular weight of between about 4000 and about 5000.

18. The composition of claim 15 wherein the surface active compound comprises less than about 7.0 percent of the pre-shampoo normalizer.

19. The composition of claim 15 wherein the pre-shampoo normalizer has a pH of between about 4 and about 6.

20. The composition of claim 15 wherein
(i) the cationic polymer comprises between about 2 and about 4 percent by weight of the pre-shampoo normalizer;
(ii) the hydrolyzed animal protein has a molecular weight of between about 4000 and about 5000 and comprises between about 5 and about 10 percent by weight of the pre-shampoo normalizer;
(iii) the surface active compound comprises less than about 5.0 percent of the pre-shampoo normalizer; and
(iv) the pre-shampoo normalizer has a pH of between about 4 and about 6.

21. The composition of claim 20 in which the cationic polymer is ethanaminium-N,N,N-trimethyl-2[(2-methyl-1-oxo-2-propenyl)oxy]-, methylsulfate homopolymer of molecular weight between about one million and about two million.

22. A pre-shampoo normalizer composition for maintaining and improving hair quality during straightening treatments comprising, in combination about 0.25% by weight of methyl p-hydroxybenzoate; about 1% by weight of N-(2-hydroxyethyl)-N-acetyl ethanolamine; about 2% by weight of an acid species; about 1% by weight of polyethylene glycol (60) lanolin; about 3% by weight of ethanaminium, N,N,N-trimethyl-2[(2-methyl-1-oxo-2-propenyl)oxy]-, methylsulfate, homopolymer; about 0.5% by weight of panthenol; about 0.5% by weight of imidazolidinyl urea; about 1% by weight of aloe vera; about 7.5% by weight of hydrolyzed animal protein; about 0.25% by weight of N-(3-chloroallyl) hexaminium chloride; about 0.75% by weight of hydroxyethyl cellulose; about 4% by weight of N,N',N'-tris(2-hydroxyethyl)-N-tallow-1,3-diaminopropane; about 4% by weight of 3-[(3-cocamidopropyl)dimethylammonio] 2-hydroxypropane sulfonate; and a sufficient quantity of water.

* * * * *